(12) United States Patent
Beeman

(10) Patent No.: US 7,926,661 B2
(45) Date of Patent: Apr. 19, 2011

(54) SELF-CONTAINED, PORTABLE KIT FOR CARRYING PERSONAL ITEMS

(76) Inventor: William Beeman, Cornwall, CT (US)

( * ) Notice: Subject to any disclaimer, the term of this patent is extended or adjusted under 35 U.S.C. 154(b) by 233 days.

(21) Appl. No.: 12/290,221

(22) Filed: Oct. 28, 2008

(65) Prior Publication Data

US 2009/0152159 A1 Jun. 18, 2009

(51) Int. Cl.
*B65D 69/00* (2006.01)
(52) U.S. Cl. .......... 206/572; 53/443; 206/231; 206/232; 206/473
(58) Field of Classification Search .......... 206/569–572, 206/232, 472, 473, 478, 479, 231; 53/443, 53/445, 467, 468, 473
See application file for complete search history.

(56) References Cited

U.S. PATENT DOCUMENTS

| 2,107,180 | A |   | 1/1936  | Gihon ............................. 190/48 |
| 2,648,366 | A | * | 8/1953  | Higbee et al. ................. 206/570 |
| 2,804,969 | A | * | 9/1957  | Barnett ......................... 206/570 |
| 5,833,330 | A | * | 11/1998 | Kos ............................... 206/570 |
| D419,300  | S |   | 1/2000  | Livingston .................... D3/284 |
| D434,901  | S |   | 12/2000 | Eskandry ...................... D3/284 |
| D441,190  | S |   | 5/2001  | Eskandry ...................... D3/289 |
| 6,779,665 | B2| * | 8/2004  | Bolanos ........................ 206/569 |
| D552,348  | S |   | 10/2007 | Martin .......................... D3/265 |
| 7,565,979 | B1| * | 7/2009  | Gibson ......................... 206/570 |
| 2003/0196929 | A1 | * | 10/2003 | Gopinathan ................ 206/570 |
| 2006/0006097 | A1 | * | 1/2006 | Peacock ....................... 206/828 |
| 2006/0293577 | A1 | * | 12/2006 | Morrison et al. ............ 206/569 |

* cited by examiner

*Primary Examiner* — Luan K Bui

(57) ABSTRACT

A self-contained portable kit that provides the convenience and ability to easily carry various items of personal value, sentimental value or necessity that bring comfort to the user of the kit, or other items for a variety of uses that are specific and personal to the user. The kit contains a closable, folding wallet having a plurality of sealable containers and a pricking device removably fastened to an inner surface of the wallet for storing a variety of items or substances. A closable pocket is coupled to another inner surface of the wallet for storing a variety of items. A method for producing the self-contained portable kit is also provided.

28 Claims, 4 Drawing Sheets

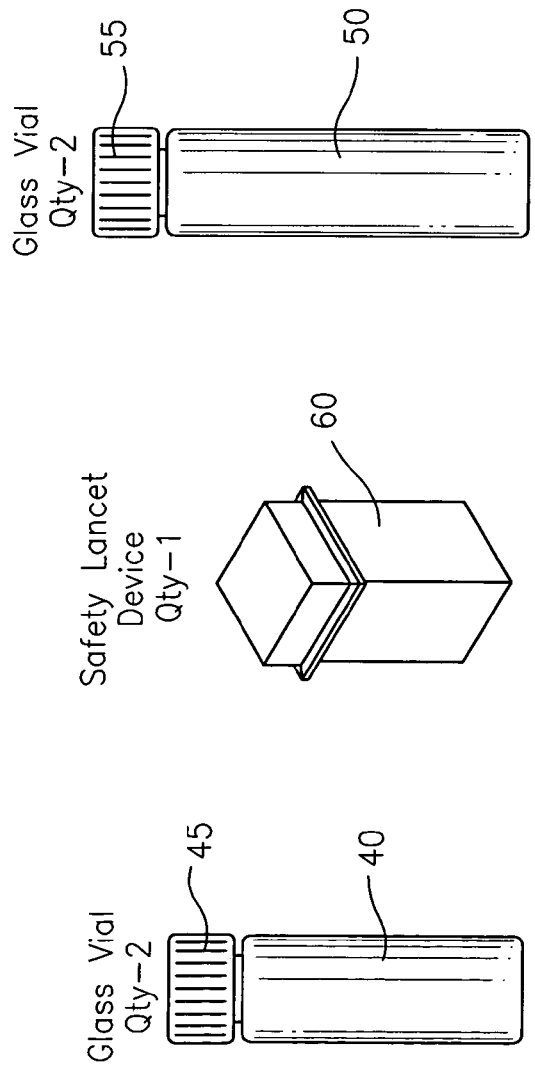
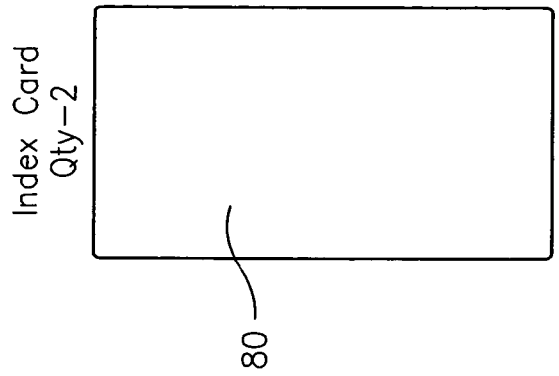
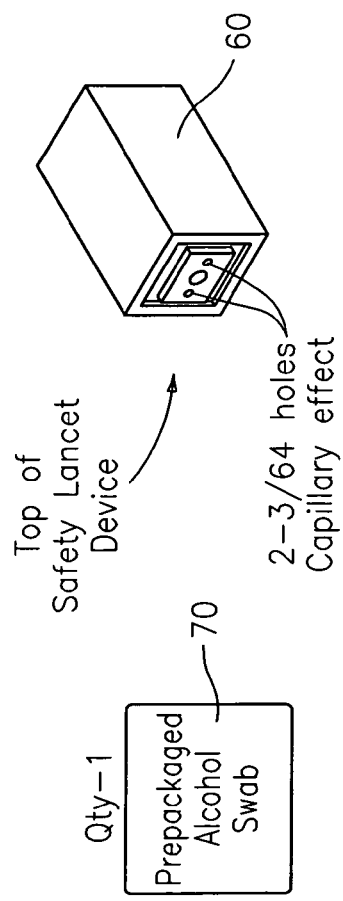

SELF-CONTAINED, PORTABLE KIT FOR CARRYING PERSONAL ITEMS

BACKGROUND OF THE INVENTION

1. Technical Field

This disclosure pertains to self-contained portable kits for carrying personal items. The kits are comprised of multiple parts that can contain various items of personal value, sentimental value or necessity.

2. Discussion of Related Art

Portable kits are known in the art for combining various related items to be used in a convenient and transportable manner for a variety of reasons. Such types of known kits include emergency medical kits, bee sting treatment kits, manicure kits, travel game kits, and the like.

There are currently no known portable kits that allow the user of the kit to personalize the contents of the kit in any manner desired. What is needed is a portable kit that provides the convenience and ability to easily carry various personal items of sentimental value that bring comfort to the user of the kit, or other items for a variety of uses that are specific and personal to the user.

DISCLOSURE OF INVENTION

Accordingly, in accordance with a first broad aspect of the invention, a portable kit for storage of personal items is provided, comprising a foldable wallet having a plurality of stabilizing fasteners coupled to a first inner surface of the wallet and a closable pocket coupled to a second inner surface of the wallet. The kit also comprises a plurality of sealable containers for coupling to the plurality of stabilizing fasteners and dimensionally sized to fit inside the wallet and a pricking device configured to produce a droplet of blood from a person's finger. The kit further comprises a set of instructions for using the portable kit dimensionally sized to fit into the closable pocket inside the wallet.

In some embodiments, the kit comprises at least one closable fastener located on an outer surface of the wallet. In some embodiments, the kit comprises a plurality of cards dimensionally sized to fit inside the closable pocket. In some embodiments, the pricking device is a lancet. In some embodiments, the pricking device is a pin or needle. In some embodiments, the kit comprises a sealed alcohol swab packet dimensionally sized to fit inside the closable pocket. In some embodiments, the wallet is comprised of a durable, flexible synthetic material. In some embodiments, the wallet is comprised of a leather material. In some embodiments, the at least one closable fastener located on the outer surface of the wallet comprises a zipper. In some embodiments, the at least one closable fastener located on the outer surface of the wallet comprises snap means. In some embodiments, the at least one closable fastener located on the outer surface of the wallet comprises hook and loop means. In some embodiments, the plurality of sealable containers are vials having screw-top closing means. In some embodiments, the vials are comprised of glass. In some embodiments, the vials are comprised of a durable synthetic material. In some embodiments, the plurality of stabilizing fasteners coupled to the inner surface of the wallet comprise hook and loop means. In some embodiments, the plurality of cards includes a suggestion card. In some embodiments, the closable pocket comprises at least one closable fastener located on an inner surface of a flap and an outer surface of the closable pocket. In some embodiments, the at least one closable fastener comprises hook and loop means. In some embodiments, the at least one closable fastener comprises snap means. In some embodiments, the set of instructions is provided on a card or sheet. In some embodiments, the set of instructions comprises steps for pricking the person's finger in order to produce a droplet of blood, introducing the droplet of blood into one of the plurality of sealable containers, wherein the introducing comprises directly dropping the droplet of blood into one of the plurality of sealable containers, placing the droplet of blood onto a tissue and introducing the tissue into one of the plurality of sealable containers, or placing the droplet of blood onto a test strip and introducing the test strip into one of the plurality of sealable containers.

In accordance with a second broad aspect of the invention, a method for assembling a portable kit is provided, the method comprising providing a foldable wallet having a plurality of stabilizing fasteners coupled to a first inner surface of the wallet and a closable pocket coupled to a second inner surface of the wallet, coupling to the plurality of stabilizing fasteners a plurality of sealable containers dimensionally sized to fit inside the wallet, providing a pricking device configured to produce a droplet of blood from a person's finger, and providing a set of instructions for using the portable kit dimensionally sized to fit into the closable pocket inside the wallet.

In some embodiments, the method further comprises introducing into the closable pocket a plurality of cards dimensionally sized to fit inside the closable pocket. In some embodiments, the method further comprises introducing into the closable pocket a sealed alcohol swab packet dimensionally sized to fit inside the closable pocket. In some embodiments, the method further comprises introducing a desired substance into each of the plurality of sealable containers. In some embodiments, the method further comprises introducing printed text or images onto each of the plurality of cards. In some embodiments, the method further comprises removing an alcohol swab from the alcohol swab packet and using the alcohol swab to sterilize the person's finger from whom blood is to be produced using the pricking device. In some embodiments, the method further comprises using the pricking device to produce blood from person's finger, wherein the blood is introduced into one of the plurality of sealable containers.

BRIEF DESCRIPTION OF THE DRAWINGS

The above and other objects, features and advantages of the invention will become apparent from a consideration of the subsequent detailed description presented in connection with accompanying drawings, in which:

FIG. 3A is a schematic representation of a vial included in the portable kit in an embodiment of the present invention.

FIG. 3B is a schematic representation of a sealable container included in the portable kit in an embodiment of the present invention.

FIG. 3C is a schematic representation of a safety lancet device included in the portable kit in an embodiment of the present invention.

FIG. 3D is a schematic representation of a safety lancet device included in the portable kit in an embodiment of the present invention.

FIG. 3E is a schematic representation of an alcohol swab packet included in the portable kit in an embodiment of the present invention.

FIG. 3F is a schematic representation of an index card included in the portable kit in an embodiment of the present invention.

FIG. 5 shows an example of an instruction card of an embodiment of the portable kit of the present invention.

FIG. 6 is a flowchart showing the steps of the method of an embodiment of the present invention.

DETAILED DESCRIPTION

Figure 1:
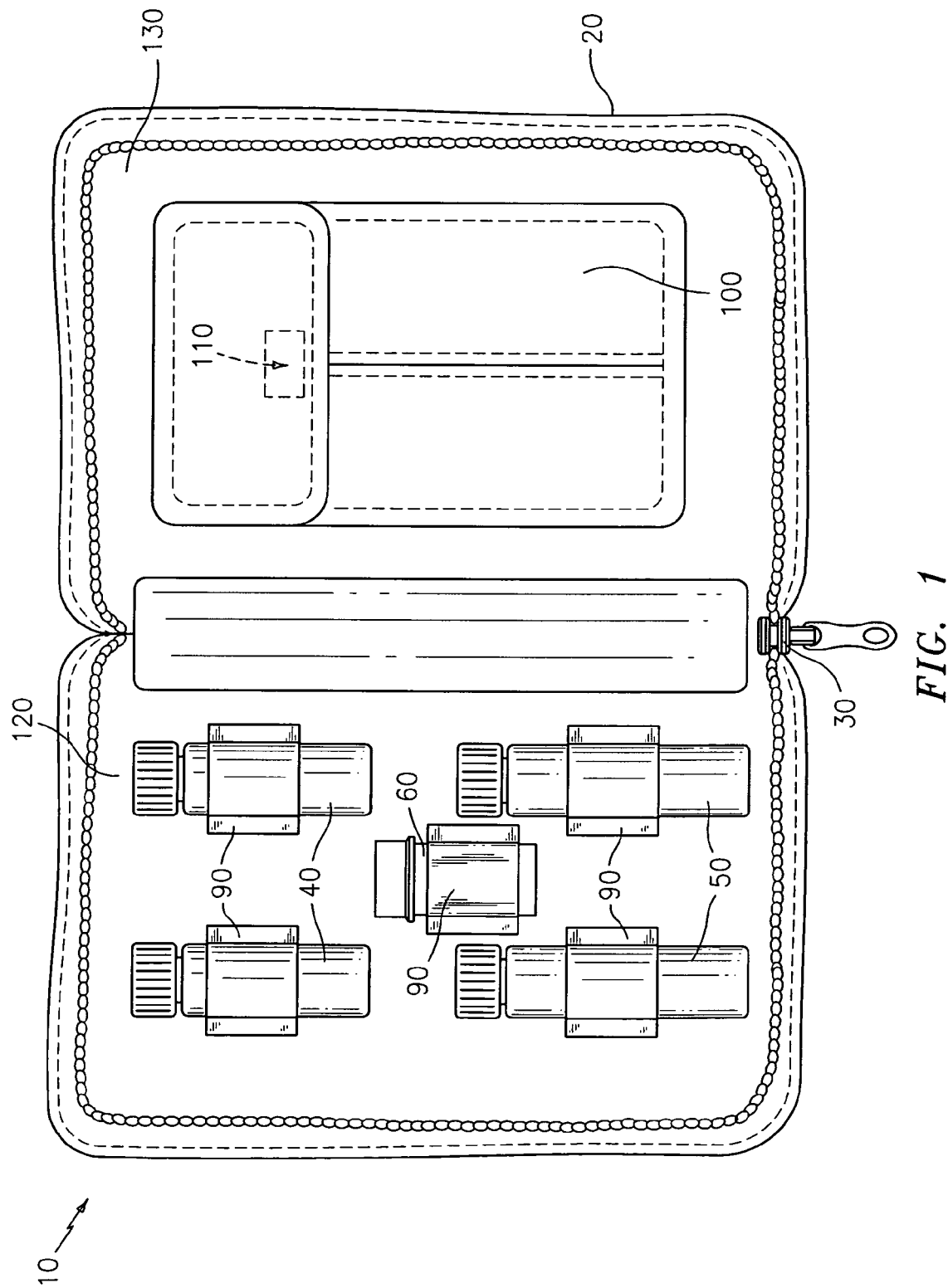
FIG. 1 is a schematic representation of the internal portions of the portable kit of the present invention, with its removable contents.

As shown in FIG. 1, a portable kit for storage of personal items is provided, comprising a foldable wallet having a plurality of stabilizing fasteners coupled to a first inner surface of the wallet and a closable pocket coupled to a second inner surface of the wallet, a plurality of sealable containers for coupling to the plurality of stabilizing fasteners and dimensionally sized to fit inside the wallet, a pricking device configured to produce a droplet of blood from a person's finger, and a set of instructions for using the portable kit dimensionally sized to fit into the closable pocket inside the wallet.

According to some embodiments, the present invention provides a portable kit that allows the user of the kit to personalize the contents of the kit in any manner desired. The portable kit provides the convenience and ability to easily carry various personal items of sentimental value that bring comfort to the user of the kit, or other items for a variety of uses that are specific and personal to the user. Some possible uses for the kit include a person preparing his or her own kit for his or her own burial, an active-duty soldier carrying his or her own personal memorable items in a pocket of his or her uniform to bring comfort in knowing he or she has a closer connection to a loved one back home, a person placing the kit containing personal memorable items into the casket of a deceased loved one to aid in the relief of grief. The scope of the invention is not intended to be limited to these uses, as will become readily apparent from the description herein.

FIG. 1 shows by way of example a portable kit generally designated 10 in an open position such that the internal structure of the kit 10 is viewed. The kit 10 is generally comprised of a wallet 20, which may be fabricated from a durable synthetic material, leather, or a similar material. The wallet 20 is closed using a closable fastener 30, which may be a zipper, snap means, hook and loop means, or any other fastening means. For illustrative purposes only, an example of such a wallet is the Fridge-to-go® Travel Wallet by KADO Industrial Company Limited, and example of such hook and loop means is the Velcro® brand Hook and Loop Sew on Tape by Velcro Industries B.V. The scope of the invention is not intended to be limited to any particular materials or fastening means using technology now known or developed in the future. In FIG. 1, kit 10 is shown with small vials 40, large vials 50, and a safety lancet device 60 securely fastened to the kit 10 via a plurality of stabilizing fasteners 90. Index cards 80 (not shown) and alcohol swab packet 70 (not shown) are inserted into a closable pocket 100. The scope of the invention is not intended to be limited to the arrangement of the inner contents of kit 10 shown in FIG. 1.

Various items may be placed in vials 40 and 50, such as water from a favorite stream or other body of water, sand from a beach, dirt from one's homestead or memorable place, a treat to give to a pet, edible snacks, cigarettes, matches, or anything else that can fit into the vials 40 and 50 by any means, such as by crushing or pulverizing. Besides the alcohol swab packet 70 and the index cards 80, various other items may be placed in the closable pocket 100, such as a tear-stained tissue, a photograph, a note from a special person, a next-life suggestion for god, or anything else that can fit into the closable pocket 100. The index cards 80 may have any manner of text or picture printed, written or drawn on them, such as a favorite poem, contact information, a suggestion list for using the kit or instructions for using the kit 10, such as instruction card 150 shown in FIG. 5 by way of example. Furthermore, the safety lancet device 60 may be used to extract a droplet of blood from a person's finger such that the blood may be placed into one of the vials 40 or 50, or otherwise deposited onto a tissue or other material, such as test strips, that can be placed into one of the vials 40 or 50 or placed into the closable pocket 100. In an alternative embodiment, the blood may also be stored in the lancet device using a capillary effect, rather than placing the blood in one of the vials. In another alternative embodiment, rather than using a lancet device, a droplet of blood may be extracted using a standard diabetic lance, a pin, a needle or any other pricking mechanism that can be sterilized. Such use of a person's blood may be for remembrance of a loved one, as part of a "blood brothers" style pact, or for various other psychological or personal reasons. The scope of the invention is not intended to be limited to any of the particular contents or uses of kit 10 described herein.

Figure 2:
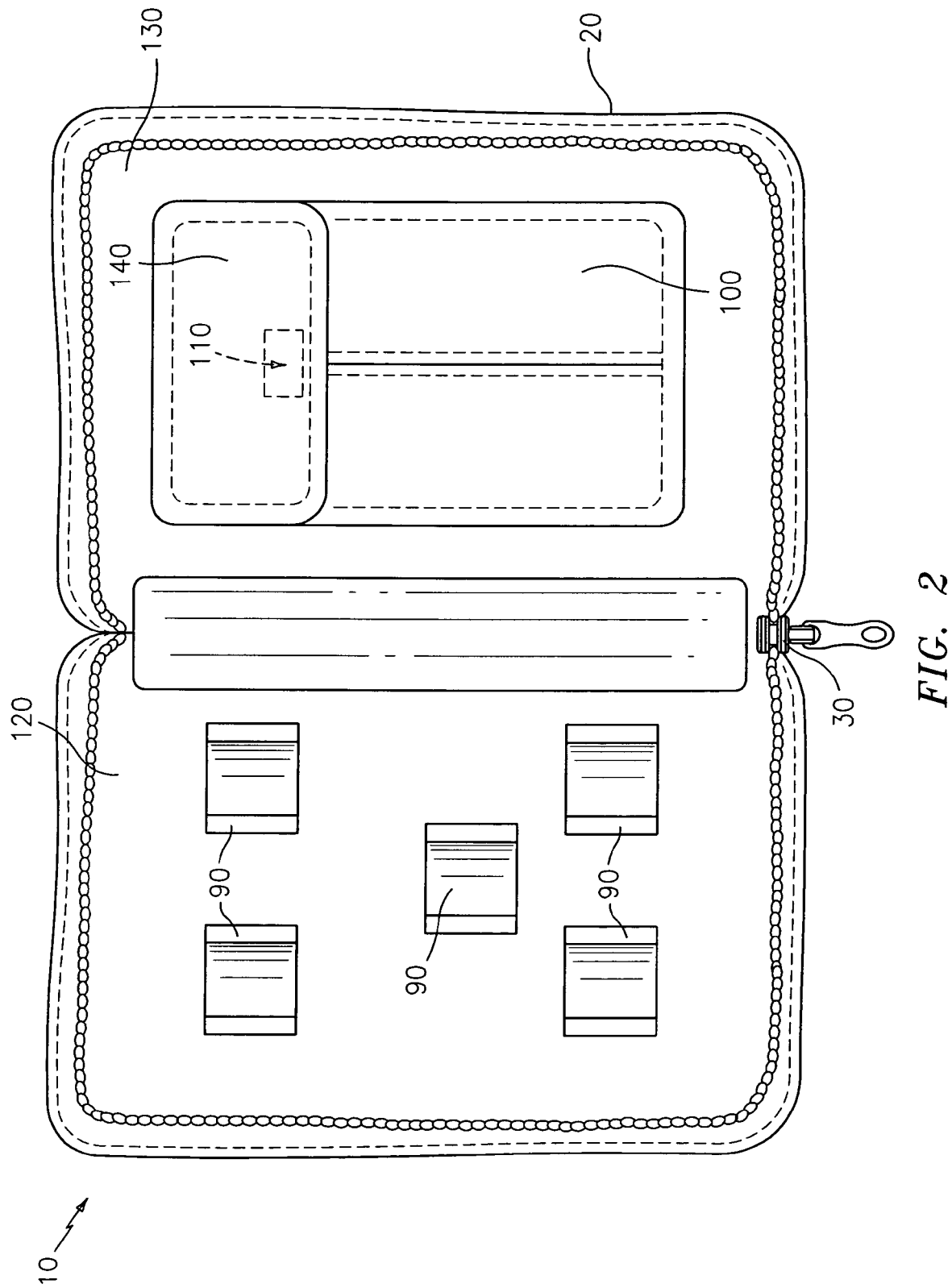
FIG. 2 is a schematic representation of the internal portions of the portable kit of the present invention, without its removable contents.

FIG. 2 shows by way of example the kit 10 in an open position such that the internal structure of the kit 10, without removable contents, is viewed. Closable fastener 30 is opened, in this embodiment unzipped, such that wallet 20 is in a flat, open position. On one inner surface 120, stabilizing fasteners 90 are coupled to the wallet 20. The stabilizing fasteners 90 may be coupled to the wallet 20 by sewing, gluing, or other attachment means. The stabilizing fasteners 90 coupled to the wallet may comprise hook and loop means. The stabilizing fasteners 90 are arranged in a manner such that several items may be placed in the wallet 20 to maximize storage space. The scope of the invention is not intended to be limited to the arrangement of the stabilizing fasteners 90 shown in FIG. 2.

On another inner surface 130, a closable pocket 100 is coupled to the wallet 20. The closable pocket 100 may be coupled to the wallet 20 by sewing, gluing, or other attachment means. The closable pocket 100 is dimensionally sized such that several items may be placed in the closable pocket 100 to maximize storage space. Closable pocket 100 has a flap 140 with closing means 110. Closing means 110 may be snap means, hook and loop means, or any other fastening means. Closing means 110 may be coupled to the flap 140 by sewing, gluing, or other attachment means. The scope of the invention is not intended to be limited to the size of the closable pocket 100 shown in FIG. 2, nor to any particular fastening means using technology now known or developed in the future.

FIGS. 3A-3F show by way of example the removable components of the kit 10 that are to be inserted into the kit 10 shown in FIG. 2. The present invention provides for various sealable containers to be inserted into the kit 10. In some embodiments, the sealable containers are vials. FIG. 3A shows a small vial 40 with a screw top 45. FIG. 3B shows a large vial 50 with a screw top 55. For illustrative purposes only, an example of such a vial is the 2 Dram Amber Glass Vial with Black Cone Lined Closure by SKS Bottle and Packaging, Inc.

FIGS. 3C and 3D show side and top views of a safety lancet device 60. For illustrative purposes only, an example of such a safety lancet device is the SurgiLance® SLB200 Safety Lancet by MediPurpose®. FIG. 3E shows an alcohol swab packet 70. For illustrative purposes only, an example of such an alcohol swab packet is the BD® Alcohol Swab by Becton, Dickinson and Company. FIG. 3F shows an index card 80 on which instructions for use and/or suggestions for use are printed. For illustrative purposes only, an example of such an index card is the Oxford® Index Card by Esselte®. The scope of the invention is not intended to be limited to any particular size, shape or material for any of the removable components of kit 10 using technology now known or developed in the future.

Figure 4A:
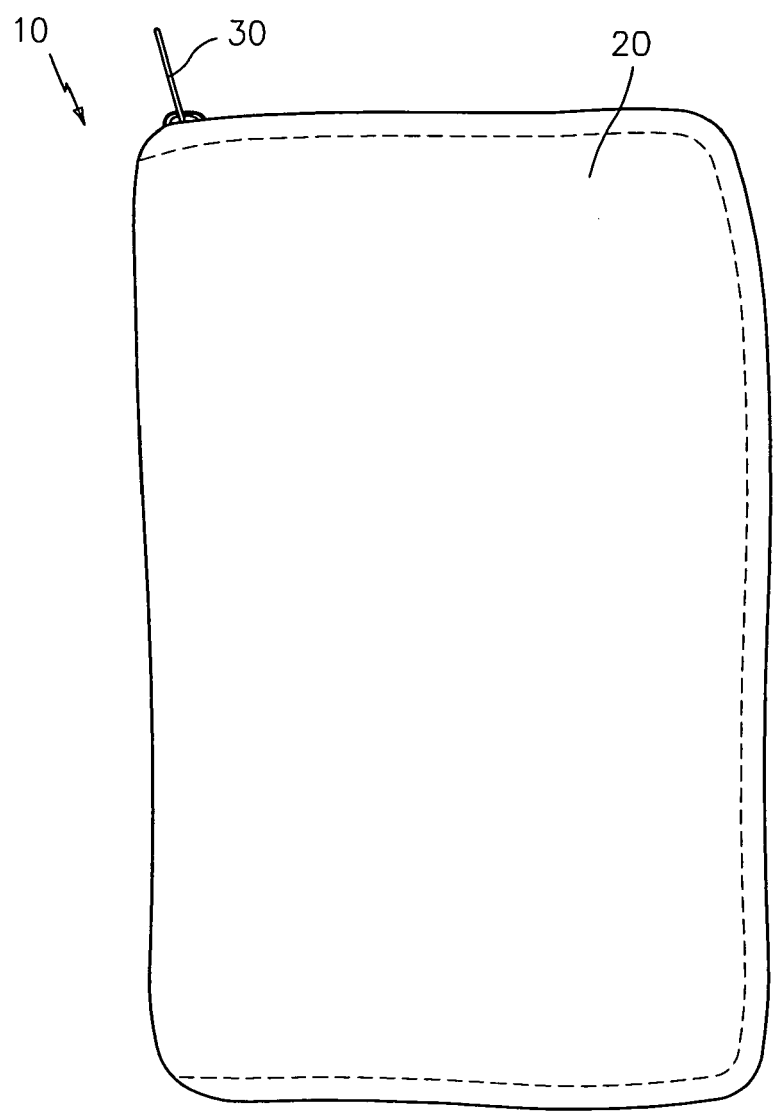
FIG. 4A shows a front view of an embodiment of the external portions of the portable kit of the present invention.
Figure 4B:
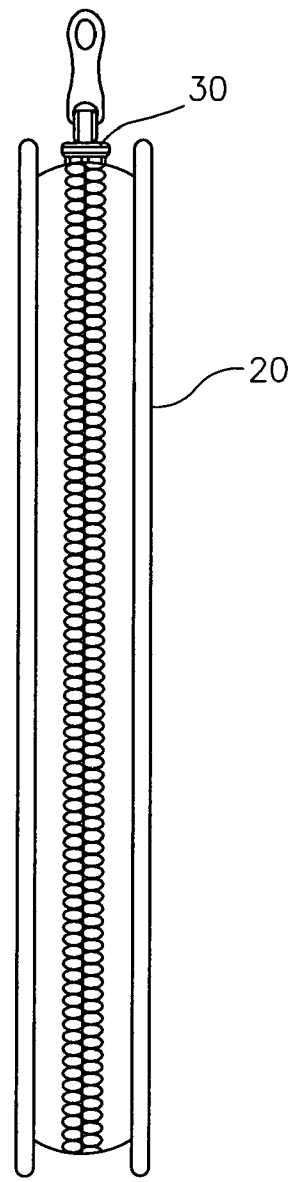
FIG. 4B shows a side view of an embodiment of the external portions of the portable kit of the present invention.

FIGS. 4A and 4B show by way of example the kit generally designated 10; front and side views are shown. The kit 10 is generally comprised of a wallet 20, which may be fabricated from a durable synthetic material, leather, or a similar material. The wallet 20 is closed using a closable fastener 30, which may be a zipper, snap means, hook and loop means, or any other fastening means. For illustrative purposes only, an example of such a wallet is the Fridge-to-go® Travel Wallet by KADO Industrial Company Limited, and example of such hook and loop means is the Velcro® brand Hook and Loop Sew on Tape by Velcro Industries B.V. The scope of the invention is not intended to be limited to any particular materials or fastening means using technology now known or developed in the future.

FIG. 6 shows by way of example a flowchart generally designated as 160 having basic steps or actions 160*a*, 160*b*, . . . 160*k* for implementing the inventive method according to some embodiments of the present invention. For example, in the inventive method according to some embodiments of the present invention, a foldable wallet is provided (step 160*a*), a plurality of stabilizing fasteners are coupled to a first inner surface of the wallet (step 160*b*), a plurality of sealable containers dimensionally sized to fit inside the wallet are coupled to the plurality of stabilizing fasteners (step 160*c*), a closable pocket is coupled to a second inner surface of the wallet (step 160*d*), a pricking device configured to produce a droplet of blood from a person's finger is provided (step 160*e*), a set of instructions for using the portable kit dimensionally sized to fit into the closable pocket inside the wallet is provided (step 160*f*), a sealed alcohol swab packet is introduced into the closable pocket (step 160*g*), a desired substance is introduced into each of the plurality of sealable containers (step 160H), a plurality of cards are introduced into the closable pocket (step 160*i*), an alcohol swab is removed from the alcohol swab packet to sterilize a person's finger from whom blood is to be produced (step 160*j*), the pricking device is used to produce blood from the person's finger and the blood is introduced into one of the plurality of sealable containers (step 160*k*). Alternatively, the blood may be stored in the lancet device via a capillary effect, thereby removing the need to place the blood into one of the plurality of sealable containers. The scope of the invention is not intended to be limited to the order in which the steps or actions in FIG. 6 are performed. It is to be understood that the aforementioned method may include other steps or actions known in the art that do not form a part of the underlying invention. Further, the scope of the invention is not intended to be limited to any particular implementation using technology now known or developed in the future for assembling and arranging a kit as disclosed.

It is to be understood that the above-described arrangements are only illustrative of the application of the principles of the present invention. Numerous modifications and alternative arrangements may be devised by those skilled in the art without departing from the scope of the present invention, and the appended claims are intended to cover such modifications and arrangements. Further, the invention contemplates all embodiments that may be inferred directly or indirectly from the disclosure and drawings whether or not expressly stated and claimed.

What is claimed is:

1. A portable kit for storage of personal items, comprising:
 a foldable wallet having a plurality of stabilizing fasteners coupled to a first inner surface of the wallet and a closable pocket coupled to a second inner surface of the wallet,
 a plurality of sealable containers for coupling to the plurality of stabilizing fasteners and dimensionally sized to fit inside the wallet,
 a pricking device configured to produce a droplet of blood from a person's finger coupled to at least one of the plurality of stabilizing fasteners, and
 a set of instructions for using the portable kit dimensionally sized to fit into the closable pocket inside the wallet,
 wherein the plurality of stabilizing fasteners coupled to the first inner surface of the wallet comprise hook and loop means.

2. The portable kit of claim 1, further comprising:
 at least one closable fastener located on an outer surface of the wallet.

3. The portable kit of claim 1, further comprising:
 a plurality of cards dimensionally sized to fit inside the closable pocket.

4. The portable kit of claim 1, wherein the pricking device is a lancet.

5. The portable kit of claim 1, wherein the pricking device is a pin or needle.

6. The portable kit of claim 1, further comprising:
 a sealed alcohol swab packet dimensionally sized to fit inside the closable pocket.

7. The portable kit of claim 1, wherein the wallet is comprised of a durable, flexible synthetic material.

8. The portable kit of claim 1, wherein the wallet is comprised of a leather material.

9. The portable kit of claim 2, wherein the at least one closable fastener located on the outer surface of the wallet comprises a zipper.

10. The portable kit of claim 2, wherein the at least one closable fastener located on the outer surface of the wallet comprises snap means.

11. The portable kit of claim 2, wherein the at least one closable fastener located on the outer surface of the wallet comprises hook and loop means.

12. The portable kit of claim 1, wherein the plurality of sealable containers are vials having screw-top closing means.

13. The portable kit of claim 12, wherein the vials are comprised of glass.

14. The portable kit of claim 12, wherein the vials are comprised of a durable synthetic material.

15. The portable kit of claim 1, wherein said pricking device is a lancet device comprising a capillary effect, so that said lancet device is also one of said plurality of sealable containers.

16. The portable kit of claim 3, wherein the plurality of cards includes a suggestion card.

17. The portable kit of claim 1, wherein the closable pocket comprises at least one closable fastener located on an inner surface of a flap and an outer surface of the closable pocket.

18. The portable kit of claim 17, wherein the at least one closable fastener comprises hook and loop means.

19. The portable kit of claim 17, wherein the at least one closable fastener comprises snap means.

20. The portable kit of claim 1, wherein the set of instructions is provided on a card or sheet.

21. The portable kit of claim 1, wherein the set of instructions comprises steps for:
   pricking the person's finger in order to produce a droplet of blood;
   introducing the droplet of blood into one of the plurality of sealable containers, wherein the introducing comprises
   directly dropping the droplet of blood into one of the plurality of sealable containers,
   placing the droplet of blood onto a tissue and introducing the tissue into one of the plurality of sealable containers, or
   placing the droplet of blood onto a test strip and introducing the test strip into one of the plurality of sealable containers.

22. A method for assembling a portable kit, comprising:
   providing a foldable wallet having a plurality of stabilizing fasteners coupled to a first inner surface of the wallet and a closable pocket coupled to a second inner surface of the wallet,
   coupling to the plurality of stabilizing fasteners a plurality of sealable containers dimensionally sized to fit inside the wallet,
   providing a pricking device configured to produce a droplet of blood from a person's finger coupled to at least one of the plurality of stabilizing fasteners, and
   providing a set of instructions for using the portable kit dimensionally sized to fit into the closable pocket inside the wallet,
   wherein the plurality of stabilizing fasteners coupled to the first inner surface of the wallet comprise hook and loop means.

23. The method of claim 22, further comprising:
   introducing into the closable pocket a plurality of cards dimensionally sized to fit inside the closable pocket.

24. The method of claim 22, further comprising:
   introducing into the closable pocket a sealed alcohol swab packet dimensionally sized to fit inside the closable pocket.

25. The method of claim 22, further comprising introducing a desired substance into each of the plurality of sealable containers.

26. The method of claim 23, further comprising introducing printed text or images onto each of the plurality of cards.

27. The method of claim 24, further comprising removing an alcohol swab from the alcohol swab packet and using the alcohol swab to sterilize the person's finger from whom blood is to be produced using the pricking device.

28. The method of claim 27, further comprising using the pricking device to produce blood from the person's finger, wherein the blood is introduced into one of the plurality of sealable containers.

* * * * *